United States Patent [19]

Nelson

[11] Patent Number: 4,638,100
[45] Date of Patent: Jan. 20, 1987

[54] AROMATIC OR INTER-OXA 2-DECARBOXY-2-HYDROXYMETHYL-PGFα COMPOUNDS

[75] Inventor: Norman A. Nelson, Charleston Township, Kalamazoo County, Mich.

[73] Assignee: The Upjohn Company, Kalamazoo, Mich.

[21] Appl. No.: 783,048

[22] Filed: Sep. 30, 1985

Related U.S. Application Data

[60] Continuation of Ser. No. 329,081, Dec. 9, 1981, abandoned, which is a continuation of Ser. No. 914,330, Jun. 5, 1978, abandoned, which is a continuation of Ser. No. 822,022, Aug. 5, 1977, abandoned, which is a continuation of Ser. No. 822,021, Aug. 5, 1977, abandoned, which is a continuation of Ser. No. 822,032, Aug. 5, 1977, abandoned, which is a continuation of Ser. No. 822,304, Aug. 5, 1977, abandoned, which is a division of Ser. No. 647,357, Jan. 8, 1976, Pat. No. 4,055,602, and a continuation of Ser. No. 778,646, Mar. 17, 1977, abandoned, and a continuation of Ser. No. 778,648, Mar. 17, 1977, abandoned, which is a division of Ser. No. 647,363, Jan. 8, 1976, Pat. No. 4,028,419.

[51] Int. Cl.$^4$ .................................... C07C 43/205
[52] U.S. Cl. ............................................. 568/645
[58] Field of Search ................................... 568/645

[56] References Cited

U.S. PATENT DOCUMENTS

| | | | |
|---|---|---|---|
| 3,810,943 | 5/1974 | Jones et al. | 568/838 X |
| 3,852,377 | 12/1974 | Bergstrom et al. | |
| 3,864,387 | 2/1975 | Nelson . | |
| 3,962,312 | 6/1976 | Hayashi et al. | 424/308 X |
| 4,028,397 | 6/1977 | Schaub et al. | 568/838 X |
| 4,055,602 | 10/1977 | Nelson | 560/60 X |
| 4,060,534 | 11/1977 | Bundy . | |

OTHER PUBLICATIONS

Karim (I), The Prostaglandins: Progress in Research (1972) 1–46.
Rosenthale et al., Advances in Prostaglandin and Thromboxane Research, vol. 1 (1976), 477–493.
Pike et al., Nobel Symposium 2: 161 (1967), 161–171.

*Primary Examiner*—Bernard Helfin
*Attorney, Agent, or Firm*—Robert A. Armitage

[57] ABSTRACT

The present invention comprises certain aromatic and inter-oxa analogs of the prostaglandins in which the C-1 carboxyl is replaced by a primary alcohol. These prostaglandin Fα analogs exhibit prostaglandin Fα activity and are accordingly useful for the same pharmacological purposes as the corresponding prostaglandins.

1 Claim, No Drawings

AROMATIC OR INTER-OXA 2-DECARBOXY-2-HYDROXYMETHYL-PGFα COMPOUNDS

CROSS REFERENCE TO RELATED APPLICATIONS

This application is a continuation of U.S. Ser. No. 329,081 filed Dec. 9, 1981, which is a continuation of U.S. Ser. No. 914,330 filed June 5, 1978, which is a continuation of U.S. Ser. No. 822,022, filed Aug. 5, 1977, a continuation of U.S. Ser. Nos. 822,021, 822,032, and 822,304, all now abandoned and all filed Aug. 5, 1977, all of which are divisional applications of U.S. Ser. No. 647,357, filed Jan. 8, 1976, now issued as U.S. Pat. No. 4,055,602, and a continuation of U.S. Ser. Nos. 778,646, and 778,648, filed Mar. 17, 1977, and both now abandoned which are divisions of U.S. Ser. No. 647,363, filed Jan. 8, 1976, now U.S. Pat. No. 4,028,419.

BACKGROUND OF THE INVENTION

The present application relates to novel aromatic or inter-oxa 2-decarboxy-2hydroxymethyl prostaglandin Fα compounds.

PRIOR ART

Several 2-decarboxy-2-hydroxymethyl prostaglandin F analogs are known in the art. See Crabbe, et al., Intra-Science Chemical Report 6:55 (1972) which discloses 2-decarboxy-2-hydroxymethyl-PGF$_{2\alpha}$. See also Fried, J. et al., Annals of the New York Academy of Sciences 180:38 (1971) which discloses 2-decarboxy-2-hydroxymethyl-13,14-didehydro-(15RS)-PGF$_{1\alpha}$. Finally, see Pike, et al., Nobel Symposium 2:161 (1967) which discloses 2-decarboxy-2-hydroxymethyl-PGF$_{1\alpha}$. U.S. Pat. No. 3,962,312 discloses 2-decarboxy-2-hydroxymethyl-PG compounds.

Further, the following publications disclose 2-decarboxy-2-hydroxymethyl prostagladin analogs: German Offenlegungsschrift No. 2,323,127 (Derwent Farmdoc CPI No. 76109U-B); German Offenlengungsschrift No. 2,437,388 (Derwent Farmdoc CPI No. 13108W); German Offenlegungsschrift No. 2,404,653 (Derwent Farmdoc CPI No. 57272V); German Offenlegungsschrift No. 2,360,893 (Derwent Farmdoc CPI No. 45723V); Netherlands Pat. No. 7,206,361 (Derwent Farmdoc CPI No. 05789U); Netherlands Pat. No. 7,209,738 (Derwent Farmdoc CPI No. 05786U); Netherlands Pat. No. 7,306,030 (Derwent Farmdoc CPI. No. 71295U); Netherlands Pat. No. 7,313,322 (Derwent Farmdoc CPI No. 28414V); Belgian Pat. No. 815,372 (Derwent Farmdoc CPI No. 84521V); and Belgian Pat. No. 815,742 (Derwent Farmdoc CPI No. 87196V). Finally, see U.S. Pat. No. 3,852,377 which describes PGF-tetraols, and Belgian Pat. No. 722,031 (Derwent Farmdoc CPI No. 37298).

SUMMARY OF THE INVENTION

The present invention particularly relates to (a) a prostaglandin analog of formula I wherein L$_1$ is α-R$_3$:β-R$_4$, α-R$_4$:β-R$_3$ or a mixture of α-R$_3$:β-R$_4$ and α-R$_4$:β-R$_3$, wherein R$_3$ and R$_4$ are hydrogen, methyl, or fluoro, with the provisos that (1) one of R$_3$ and R$_4$ is methyl only when the other is hydrogen or methyl; and (2) one of R$_3$ and R$_4$ is fluoro only when R$_7$ is other than phenoxy, wherein M$_1$ is α-OH:β-R$_5$ or α-R$_5$:β-OH, wherein R$_5$ is hydrogen or methyl, wherein Z$_1$ is (1) —(m—Ph)—Z$_3$—(CH$_2$)$_g$—
(2) —CH$_2$—O—CH$_2$(CH$_2$)$_g$—CH$_2$—,
(3) cis—CH=CH—(CH$_2$)$_g$—CF$_2$,
(4) cis—CH$_2$—CH=CH—(CH$_2$)$_g$—CH$_2$, or
(5) —(CH$_2$)$_3$—(CH$_2$)$_g$—CF$_2$— wherein —(m—Ph)— is inter-m-phenylene, Z$_3$ is methylene or oxa, and g is one, 2 or 3, and R$_7$ is phenoxy optionally substituted by one, 2, or 3 chloro, fluoro, trifluoromethyl, (C$_1$-C$_3$) alkyl, or (C$_1$-C$_3$) alkoxy, the various substituents being the same or different with the proviso that not more than two such substituents are other than alkyl;

wherein Z$_1$ is (1) —CH$_2$—O—CH$_2$—(CH$_2$)$_g$—CH$_2$—, or
(2) —(m—Ph)—O—(CH$_2$)$_g$—, wherein —(m—Ph)— and g are as defined above and R$_7$ is —(CH$_2$)$_m$—CH$_3$, wherein m is one to 5, inclusive; and wherein Z$_1$ is —(m—Ph)—O—(CH$_2$)$_g$— and R$_7$ is benzyl optionally substituted by one, 2, or 3 chloro, fluoro, trifluoromethyl, (C$_1$-C$_3$) alkyl, or (C$_1$-C$_3$) alkoxy, the various substituents being the same or different with the proviso that not more than two such substituents are other than alkyl;

(b) a prostaglandin analog of formula II wherein g, Z$_3$, M$_1$ and L$_1$ are as defined above and wherein s is zero, one, 2, or 3 and T is chloro, fluoro, trifluoromethyl, (C$_1$-C$_3$) alkyl or (C$_1$-C$_3$) alkoxy the various T's being the same or different, with the proviso that not more than two T's are other than alkyl;

(c) a prostaglandin analog of formula III wherein g, s, M$_1$, T and L$_1$ are as defined above; and (d) a prostaglandin analog of formula IV wherein Z$_2$ is cis—CH=CH—CH$_2$—(CH$_2$)$_g$—CF$_2$—;
cis—CH$_2$—CH=CH—(CH$_2$)$_g$—CH$_2$; or
—(CH$_2$)$_3$—(CH$_2$)$_g$—CF$_2$—;

wherein g, s, M$_1$, T and L$_1$ are as defined above and (e) a prostaglandin analog of formula V wherein g, M$_1$, L$_1$ and m are as defined above;

(f) a prostaglandin analog of formula VI wherein g, M$_1$, L$_1$ and m are as defined above;

(g) a prostaglandin analog of formula VII wherein g, s, M$_1$, T and L$_1$ are as defined above.

With regard to the divalent substituents described above (e.g., L$_1$ and M$_1$), these divalent radicals are defined as α-R$_i$:β-R$_j$, wherein R$_i$ represents the substituent of the divalent moiety in the alpha configuration with respect to the plane of the C-8 to C-12 cyclopentane ring and R$_j$ represents the substituent of the divalent moiety in the beta configuration with respect to the plane of the ring. Accordingly, when M$_1$ is defined as α-OH:β-R$_5$, the hydroxy of the M$_1$ moiety is in the alpha configuration, i.e., and the R$_5$ substituent is in the beta configuration.

The carbon atom content of various hydrocarbon-containing moieties is indicated by a prefix designating the minimum and maximum number of carbon atoms in the moiety, i.e., the prefix (C$_i$-C$_j$) indicates a moeity of the integer "i" to the integer "j" carbon atoms, inclusive. Thus (C$_1$-C$_3$) alkyl refers to alkyl of one to 3 carbon atoms, inclusive, or methyl, ethyl, propyl, and isopropyl.

The preparation and use of the above compounds, including the best mode therefor, are incorporated here by reference from U.S. Pat. Nos. 4,028,419 and 4,055,602. Accordingly, these prostaglandin analogs exhibit prostaglandin Fα-like activity and are accordingly useful for the same purposes as the known prostaglandin Fα compounds. For the known PGFα compounds, these biological responses include:

(a) stimulating smooth muscle, (b) inhibiting gastric secretion and reducing undesirable gastrointestinal side effects from systemic administration of prostaglandin synthetase inhibitors, (c) decongesting nasal passages, (d) decreasing blood platelet adhesion and (e) inhibiting blood platelet aggregation and thrombis formation, and (f) affecting the reproductive organs of mammals as labor inducers, abortifacients, cervical dilators, regulators of the estrus, and regulators of the menstrual cycle. See U.S. Pat. Nos. 4,028,419 and 4,055,602, incorporated by reference, for further details of the preparation and use of these compounds in eliciting the aforementioned biological responses.

FORMULAS

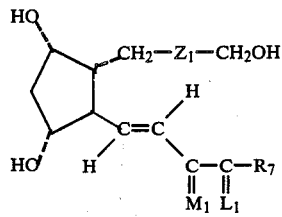
I

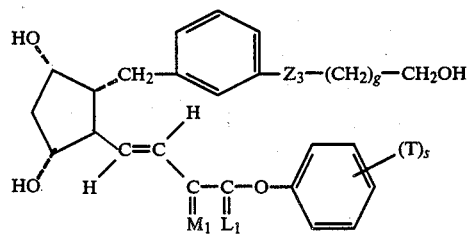
II

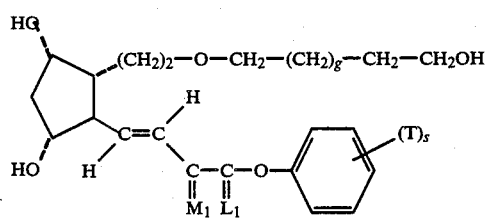
III

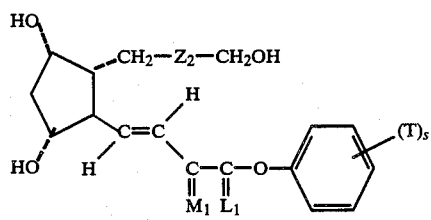
IV

-continued
FORMULAS

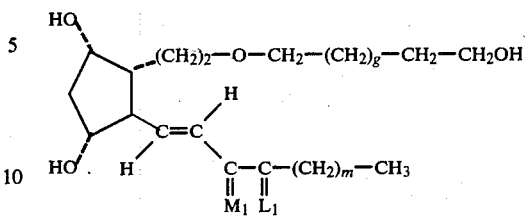
V

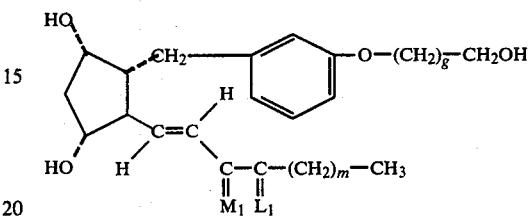
VI

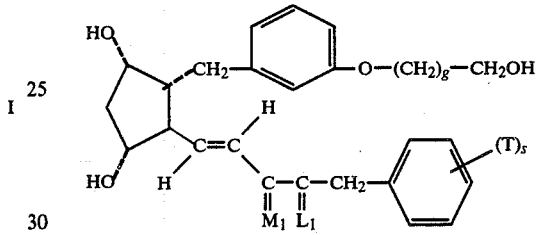
VII

I claim:
1. A prostaglandin analog of the formula

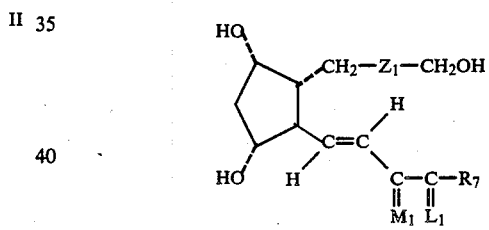

wherein $L_1'$ is, $\alpha\text{-}R_3{:}\beta\text{-}R_4$, $\alpha\text{-}R_4{:}\beta\text{-}R_3$ or a mixture of $\alpha\text{-}R_3{:}\beta\text{-}R_4$ and $\alpha\text{-}R_4{:}\beta\text{-}R_3$, wherein $R_3$ and $R_4$ are hydrogen, methyl, or fluoro, with the provisos that (1) one of $R_3$ and $R_4$ is methyl only when the other is hydrogen or methyl; and (2) one of $R_3$ and $R_4$ is fluoro only when $R_7$ is other than phenoxy, wherein $M_1$ is $\alpha\text{-}OH{:}\beta\text{-}R_5$ or $\alpha\text{-}R_5{:}\beta\text{-}OH$, wherein $R_5$ is hydrogen or methyl, wherein $Z_1$ is —(m—Ph)—$Z_3$—$(CH_2)_g$—, wherein —(m—Ph)— is inter-m-phenylene, $Z_3$ is oxa, and g is one, 2 or 3, and $R_7$ is phenoxy optionally substituted by one, 2, or 3 chloro, fluoro, trifluoromethyl, ($C_1$-$C_3$) alkyl, or ($C_1$-$C_3$) alkoxy, the various substituents being the same or different with the proviso that not more than two such substituents are other than alkyl.

* * * * *